United States Patent [19]
Arola et al.

[11] Patent Number: 5,733,567
[45] Date of Patent: Mar. 31, 1998

[54] BIODEGRADABLE, CONTROLLED-RELEASE MICROSPHERES AND PROCESS FOR PREPARING THEM

[75] Inventors: Rosa Arola; Miguel Angel Asin; Eulalia Ferret, all of Barcelone, Spain; Eric Goutay, Auzielle, France; Amadeo Perez; Pere Tarin, both of Barcelone, Spain

[73] Assignee: Pierre Fabre Medicament, Boulogne, France

[21] Appl. No.: 722,159

[22] PCT Filed: Apr. 13, 1995

[86] PCT No.: PCT/FR95/00485

§ 371 Date: Oct. 11, 1996

§ 102(e) Date: Oct. 11, 1996

[87] PCT Pub. No.: WO95/28149

PCT Pub. Date: Oct. 26, 1995

[30] Foreign Application Priority Data

Apr. 15, 1994 [FR] France .................... 94 04511

[51] Int. Cl.$^6$ ........................................ A61F 2/00
[52] U.S. Cl. .................. 424/426; 424/489; 424/9.32; 424/470; 424/424; 424/425
[58] Field of Search ................. 424/450, 457, 424/426, 425, 424, 470, 489; 423/338; 252/314

[56] References Cited

U.S. PATENT DOCUMENTS

| | | | |
|---|---|---|---|
| 5,326,484 | 7/1994 | Nakashima et al. | 252/314 |
| 5,376,347 | 12/1994 | Ipponmatsu et al. | 423/338 |
| 5,389,377 | 2/1995 | Chagnon et al. | 424/450 |

FOREIGN PATENT DOCUMENTS

| | | |
|---|---|---|
| 0481732 | 4/1992 | European Pat. Off. |
| 9325191 | 12/1993 | WIPO |
| 9325221 | 12/1993 | WIPO |

*Primary Examiner*—Thurman K. Page
*Assistant Examiner*—William E. Benston, Jr.
*Attorney, Agent, or Firm*—The Firm of Gordon W. Hueschen

[57] ABSTRACT

Method for the preparation of a pharmaceutical composition in the form of microspheres controllably releasing at least one water-soluble active ingredient. The method comprises the steps of dissolving the active ingredient in a suitable quantity of water, emulsifying the aqueous solution containing the active ingredient with a solution of at least a dl-lactide-co-glycolide-type matrix copolymer in chlorinated hydrocarbon also containing a low molecular weight polyactide release-modulating agent, which results in a first microfine and homogeneous emulsion; emulsifying the first emulsion thus obtained in an external aqueous phase containing a surface active agent; and removing and evaporating the solvent to produce microspheres which are recovered after filtering, washing, and drying. The microspheres themselves.

26 Claims, 1 Drawing Sheet

BIODEGRADABLE, CONTROLLED-RELEASE MICROSPHERES AND PROCESS FOR PREPARING THEM

This application is a 371 of PCT/FR95/00485 filed Apr. 13, 1995.

The present invention relates to the production of biodegradable microspheres based on hydrophilic, pharmacologically active compounds, enabling a controlled and sustained release of said active substance to be effected irrespective of the administration route adopted (for example administration by injection).

A large number of pharmaceutical dosage forms based on biodegradable and biocompatible polymers or copolymers have already been described in the prior art. These various forms are obtained by processes whose specificity is always closely linked:

- to the desired administration route (size, shape of the pharmaceutical dosage form),
- to the physicochemical properties of the encapsulated molecule, in particular its solubility, its thermostability and its melting point,
- to the pharmacological and pharmacodynamic properties of this active molecule.

In most applications, the ocular, dermal, auricular and oral routes, it is not necessary to develop small-sized pharmaceutical dosage forms. Accordingly, the processes of melting-extrusion, nebulization, fluidization and even tableting on a conventional tableting machine are very widely described and used.

For implantable pharmaceutical dosage forms, the manufacturing processes are also numerous, since the size of the implant does not necessitate a very large drop in particle size, and hence the processes mentioned above are to be found.

On the other hand, for dosage forms intended for parenteral administration, the manufacturing processes are very strongly linked to the following constraints:

- on the one hand the size of the pharmaceutical dosage form, which must be able to be administered in the form of an injectable suspension by a suitable syringe (18 to 22 gauge). This makes it necessary to take account of this constraint and to obtain microcapsules or microspheres smaller than 150 μm in size,
- on the other hand the physicochemical stability of the molecule and its solubility (water-soluble, fat-soluble) which conditions, for liquid-medium processes, the direction of the simple or multiple emulsions,
- and lastly the optimal pharmacokinetic profile of said dosage form, which conditions at the same time the duration of the activity of the product.

In spite of these constraints, which are sometimes very hard to overcome, there is a wide variety of microencapsulation processes, among which there may be mentioned:

emulsion-evaporation of solvent,
emulsion-extraction of solvent,
phase separation,
nebulization or spray drying,
extrusion, and
treatment in an air-fluidized bed.

The subject of the present invention relates to the production of microspheres based on a hydrophilic molecule, by a process of the multiple emulsion-evaporation of solvent type.

Generally speaking, in a process of this type entailing a W/O/W multiple emulsion and evaporation of the solvent, the water-soluble active principle is solubilized in the first place in the internal phase of a first, W/O emulsion and then, in a second stage, this first emulsion is in its turn emulsified in an external aqueous phase.

This technique has proved especially advantageous for formulating very water-soluble active principles, for which it gives a good efficiency of encapsulation.

The physical principle of multiple emulsion for encapsulating water-soluble active principles has, for example, been described in U.S. Pat. No. 3,523,906.

The present invention relates to a process for preparing a pharmaceutical composition in the form of microspheres affording controlled release of at least one water-soluble active principle, characterized by the following succession of steps:

dissolution of the active principle in a suitable amount of water, emulsification of the aqueous solution of active principle thereby obtained with a solution of at least one matrix copolymer of the dl-lactide-co-glycolide type in a chlorinated hydrocarbon containing, in addition, a release-modulating agent which is a low molecular weight polylactide, leading to a first, microfine and homogeneous emulsion, emulsification of said first emulsion thereby obtained in an external aqueous phase containing a surfactant, extraction-evaporation of the solvent to obtain microspheres which are recovered after filtration, washing and drying.

Other features and advantages will become apparent on reading the detailed description given below, in particular with the aid of a few particular examples of implementation.

This invention consists in producing pharmaceutical compositions, in the form of microspheres, intended for obtaining a controlled and sustained release of a water-soluble active principle, according to a process entailing W/O/W multiple emulsion and extraction-evaporation of the solvent, in which, according to a particular feature that consists in using a continuous evaporation system consisting of an incline of appropriate length over which the suspension of microspheres flows in a thin layer, a decrease is achieved in the length of time required.

The water-soluble active principles (I) which my be used in the context of this process comprise natural or synthetic substances endowed with pharmacological activity, such as peptides, bronchodilators, antibiotics, antidepressants, analgesics, anti-inflammatories, vaccines, and the like. Special mention will be made of the following active principles: calcitonin, vasopressin, somatostatin, growth hormone, prolactin, luteinizing hormone, oxytocin, secretin, salbutamol, gentamicin, tetracycline, tobramycin, amikacin, sodium salicylate, diclofenac sodium, amoxicillin, ampicillin, naproxen sodium, vinorelbine, vincristine, vindesine, methotrexate, cisplatin, carmustine, doxorubicin, epirubicin, daunorubicin, ifosfamide and derivatives thereof. This list of active principles merely illustrates products capable of being encapsulated by this process, without, however, other products being ruled out.

The concentrations used in the internal aqueous phase in the context of the present invention are dependent on the solubility of the active principle in water, on the characteristics of said active principle and on the sustained release, which it is desired to obtain. As an example, concentrations ranging from 0.01% to 95%, preferably between 0.05 and 50% and especially between 0.05 and 2.5% will be mentioned.

The matrix polymer(s) (II) which can be used for preparing microspheres by W/O/W must, on the one hand, be capable of being solubilized in a suitable volatile solvent (III). As examples of such solvents (III), halogenated alkanes such as methylene chloride, chloroform, chloroethane, dichloroethane, trichloroethane and carbon tetrachloride, ethyl acetate, and the like, will be mentioned. On the other hand, said polymer(s) must be water-immiscible and, lastly, be biodegradable and biocompatible with the body. Vast experience acquired with polylactide-co-glycolide copolymers demonstrates that the latter are fully tolerated by the body, and that they have a minimal inflammatory response, are absorbed without accumulating in the vital organs and are finally eliminated completely. Accordingly, the polymers chosen are polylactide-co-glycolides, especially dl-lactide-co-glycolides, in lactic/glycolic ratios of 85:15 and 40:60, preferably between 75:25 and 50:50. They afford, in effect, a faster hydrolysis rate, thereby avoiding deposition at the site of administration, after the release of the active principle. The release-modulating agent (IV) is a low molecular weight polylactide, especially a dl-lactide, which is added to the polylactide-co-glycolide copolymer in any proportions.

According to the process which is the subject of the present invention, the molecular weight of the copolymer must be between 10,000 and 500,000, preferably between 10,000 and 250,000 and advantageously between 12,000 and 34,000, while, for the release-modulating agent, the molecular weight must be between 1000 and 10,000, preferably in the region of 2000.

The concentrations and molecular weights of the polymers used are dependent on the active principle and on the desired rate of release. According to the process which is the subject of the present invention, suitable concentrations of the polymers present in the organic phase are between 5% and 50%.

The external aqueous phase (V) contains a surfactant (VI) such as polyvinyl alcohols, polyvinylpyrrolidones, polyoxyethylenesorbitan monooleate, polyoxyethylenesorbitan monolaurate, poloxamers, carboxymethylcellulose sodium or mixtures thereof. The concentrations to be used range from 0.05 to 25%. In this process, the surfactant preferably adopted is a mixture of polyvinylpyrrolidone and polyoxyethylenesorbitan monooleate.

Considered in greater detail, the process according to the invention consists in performing the following steps.

An amount of active principle (I) is prepared dissolved in one volume of purified water. This solution is emulsified, for example by means of a sonicator, in one volume of methylene chloride (III) containing a polylactide-co-glycolide copolymer (II) and the release-modulating agent (IV), namely the low molecular weight polylactide. This first emulsion must be microfine and homogeneous, which will enable the active principle to be distributed throughout the polymer matrix, ensuring the reproducibility of different batches without the need to use surfactants or other adjuvant agents. When the first emulsion has been formed, it is, in its turn, emulsified in an external phase (V) composed of an aqueous solution containing polyvinylpyrrolidone and polyoxyethylenesorbitan monooleate (VI), with stirring for a short period. After this, the preparation is diluted with purified water and the suspension is transferred to a continuous evaporation system consisting of an incline of appropriate length over which the suspension of microspheres flows in a thin layer, which improves the extraction-evaporation of the solvent and reduces the process time. The microspheres are recovered by filtration, washed with purified water and dried by lyophilization.

This process, which is simple to carry out and reproducible, enables microspheres of an appropriate size for their administration to be obtained.

An important feature of this invention lies in the fact that the addition of the low molecular weight polylactide to the polylactide-co-glycolide copolymer enables the release of the active principle to be modulated. It was found that, by increasing the proportion of low molecular weight polylactide, an increase was obtained in the rate of release of the encapsulated product (see Examples 1 and 2) which is present in the small reservoirs inside the microspheres (see Example 7).

According to an additional feature of the present invention, the ratio of the copolymer to the modulating agent is between 10:90 and 90:10, preferably between 50:50 and 90:10.

Generally speaking, the microspheres obtained in accordance with the process of the invention are always smaller than approximately 250 µm, preferably smaller than approximately 100 µm and advantageously between 3 and 40 µm.

The formation of the second emulsion is the most critical step of this process as regards the efficiency of encapsulation, most particularly if it is desired to obtain small sizes.

The novelty of the process according to the present invention enables the total time of implementation of the process to be reduced, produces an early stabilization of the polymer matrix and prevents the loss of encapsulated product. The speed of hardening of the microspheres permits a good efficiency of encapsulation even on adding a low molecular weight polylactide to the polymer solution, without it being necessary to use adjuvants in the first emulsion. Furthermore, the process is carried out at room temperature and at atmospheric pressure and, as a result, problems such as the degradation of thermolabile products or the breakage of microspheres when a vacuum is used in the extraction-evaporation step are avoided.

According to another additional feature of the present invention, the ratio between the phases of the first emulsion is between 1:100 and 25:100.

One of the essential objects of this invention is to modulate the release of the active principle by adjusting the ratio between the low molecular weight polylactide and the polylactide-co-glycolide for the production of the microspheres. This form of modulation is readily reproducible.

To ensure the reproducibility of the release (see Example 3), it is essential for the proportion of the copolymer and of the modulating agent to be maintained in the polymer matrix. It was found experimentally by NMR that there was a linear correlation between the theoretical percentage of low molecular weight poly-lactide incorporated and the actual percentage found. For each level of low molecular weight polylactide (between 0% and 90%), the results obtained are reproducible (see Example 4).

DETAILED DESCRIPTION OF THE INVENTION

EXAMPLE 1

Figure 1:
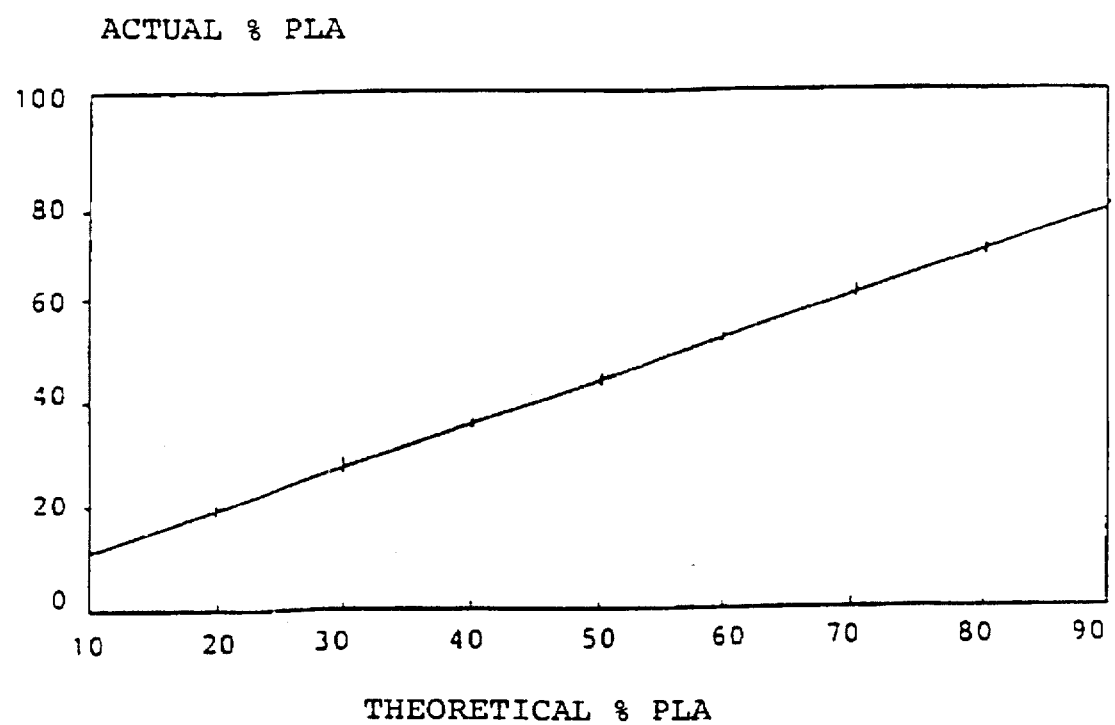
FIG. 1 is a graph showing the statistically correlated values of actual % PLA as a function of a theoretical PLA according to Example 4.

20 mg of tartrazine are dissolved in 1 ml of purified water. This solution is emulsified by means of a sonicator in 10 ml of methylene chloride containing 15% of mixture of a poly(dl-lactide-co-glycolide) 50:50 copolymer with an inherent viscosity of approximately 0.4 dl/g in $CHCl_3$ and increasing amounts of a release-modulating agent, poly(dl-lactide) of molecular weight 2000. When the first emulsion has been formed, it is emulsified in its turn in 1000 ml of aqueous solution composed of 4% polyvinylpyrrolidone and 0.25% poly-oxyethylenesorbitan monooleate, with stirring using a propeller type paddle for 90 seconds. After this, the suspension is passed through a continuous evaporation system consisting of an incline of appropriate length over which the suspension of microspheres flows in a thin layer. The microspheres are recovered by filtration, washed with purified water and dried by lyophilization.

With this process, microspheres were produced with the following proportions of low molecular weight polylactide:

| Examples | 1.1 | 1.2 | 1.3 | 1.4 | 1.5 | 1.6 |
|---|---|---|---|---|---|---|
| % polylactide | 0% | 10% | 20% | 30% | 40% | 50% |

Percentage of tartrazine released from microspheres in phosphate buffer at pH 7.4 and at 37° C. (mean of two or more values)

| Example | 4 h | 6 h | 24 h | 48 h |
|---|---|---|---|---|
| 1.1 | 4.1 | 3.9 | 5.9 | 5.3 |
| 1.2 | 9.4 | 9.6 | 12.2 | 20.6 |
| 1.3 | 27.9 | 27.8 | 36.7 | 72.6 |
| 1.4 | 30.1 | 30.5 | 47.6 | 88.3 |
| 1.5 | 51.3 | 50.6 | 73.4 | 104.2 |
| 1.6 | 79.2 | 82.6 | 97.1 | 102.2 |

EXAMPLE 2

20 mg of tartrazine are dissolved in 1 ml of purified water. This solution is emulsified by means of a sonicator in 10 ml of methylene chloride containing 20% of mixture of a poly(dl-lactide-co-glycolide) 50:50 copolymer with an inherent viscosity of approximately 0.2 dl/g in CHCl$_3$ and increasing amounts of a release-modulating agent, poly(dl-lactide) of molecular weight 2000. For the production of the microspheres, the procedure is as in Example 1.

With this process, microspheres were produced with the following proportions of low molecular weight polylactide:

| Example | 2.1 | 2.2 | 2.3 | 2.4 |
|---|---|---|---|---|
| % polylactide | 0% | 10% | 20% | 40% |

Percentage of tartrazine released from microspheres in phosphate buffer at pH 7.4 and at 37° C. (mean of two or more values)

| Example | 4 h | 6 h | 24 h | 48 h |
|---|---|---|---|---|
| 2.1 | 5.2 | 5.3 | 5.6 | 6.5 |
| 2.2 | 12.4 | 11.6 | 14.7 | 22.4 |
| 2.3 | 43.2 | 53.0 | 71.8 | 82.4 |
| 2.4 | 81.4 | 88.2 | 103.6 | 102.3 |

EXAMPLE 3

Study of reproducibility of the in vitro release of 3 formulations of Examples 1 and 2.
Percentage of tartrazine released from microspheres in phosphate buffer at pH 7.4 and at 37° C. (mean of two or more values)

| Example | 6 h | 24 h | 48 h | 72 h | 96 h |
|---|---|---|---|---|---|
| 1.4 | 31.2 | 43.6 | — | 97.8 | 99.1 |
| 1.4 | 30.5 | 47.6 | 88.3 | 100.1 | 101.8 |
| 2.2 | 14.8 | 18.3 | 21.7 | 27.3 | 36.8 |
| 2.2 | 11.6 | 14.7 | 22.4 | 32.0 | — |
| 2.3 | 53.0 | 71.8 | 82.4 | 85.1 | 89.5 |
| 2.3 | — | 77.8 | 82.1 | 92.8 | 94.5 |

EXAMPLE 4

NMR study of the reproducibility of the polymer mixture formed by the matrix of microspheres produced according to the process described in Examples 1 and 2.

| Theoretical % PLA | Actual % PLA |
|---|---|
| 10 | 8.9 |
| 20 | 16.3 |
|  | 16.9 |
|  | 15.5 |
| 30 | 24.0 |
|  | 24.6 |
| 40 | 33.1 |
|  | 35.2 |
|  | 35.0 |
|  | 34.4 |
| 50 | 44.0 |
|  | 42.4 |
|  | 42.7 |
| 60 | 52.9 |
|  | 51.5 |
|  | 51.9 |
| 70 | 59.1 |
|  | 60.5 |
|  | 59.5 |
| 80 | 69.4 |
|  | 69.8 |
|  | 68.4 |
| 90 | 78.4 |
|  | 77.7 |
|  | 77.9 |

PLA: polylactide of MW2000
The variation of the statistically correlated values of actual % PLA as a function of theoretical PLA is shown in the diagram of attached FIG. 1.

EXAMPLE 5

Production of microspheres according to the process described in Example 1, using salmon calcitonin as active principle.

EXAMPLE 5.1

7.5 mg of salmon calcitonin are dissolved in 1 ml of purified water and emulsified in 10 ml of methylene chloride containing 1500 mg of poly(dl-lactide-co-glycolide) 50:50 of inherent viscosity approximately 0.4 dl/g in CHCl$_3$. For the production of microspheres, the procedure is as in Example 1. The mean size based on area, obtained by laser light scattering, is 16.8 μm. The efficiency is 92.5%.

EXAMPLE 5.2

7.5 mg of salmon calcitonin are dissolved in 1 ml of purified water and emulsified in 10 ml of methylene chloride containing a mixture composed of 1050 mg of poly(dl-lactide-co-glycolide) 50:50 with an inherent-viscosity of approximately 0.4 dl/g in CHCl$_3$ and 450 mg of a release-modulating agent, poly(dl-lactide) of molecular weight 2000. For the production of microspheres, the procedure is as in Example 1. The mean size based on area, obtained by laser light scattering, is 22.9 μm. The efficiency is 102.5%. A photograph was taken of the microspheres selected by cryofracture, using a scanning electron microscope.

EXAMPLE 5.3

7.5 mg of salmon calcitonin are dissolved in 1 ml of purified water and emulsified in 10 ml of methylene chloride containing a mixture composed of 900 mg of poly(dl-lactide-co-glycolide) 50:50 with an inherent viscosity of approximately 0.4 dl/g in $CHCl_3$ and 600 mg of a release-modulating agent, poly(dl-lactide) of molecular weight 2000. For the production of the microspheres, the procedure is as in Example 1. The mean size based on area, obtained by laser light scattering, is 17.6 μm. The efficiency is 98.5%.

EXAMPLE 5.4.

10 mg of salmon calcitonin are dissolved in 1 ml of purified water and emulsified in 10 ml of methylene chloride containing 2000 mg of poly(dl-lactide-co-glycolide) 50:50 with an inherent viscosity of approximately 0.2 dl/g in $CHCl_3$. For the production of the microspheres, the procedure is as in Example 1. The mean size based on area, obtained by laser light scattering, is 30.4 μm. The efficiency is 92.6%.

EXAMPLE 5.5

10 mg of salmon calcitonin are dissolved in 1 ml of purified water and emulsified in 10 ml of methylene chloride containing a mixture composed of 1400 mg of poly(dl-lactide-co-glycolide) 50:50 with an inherent viscosity of approximately 0.2 dl/g in $CHCl_3$ and 600 mg of a release-modulating agent, poly(dl-lactide) of molecular weight 2000. For the production of microspheres, the procedure is as in Example 1. The mean size based on area, obtained by laser light scattering, is 36.2 μm. The efficiency is 106.5%.

EXAMPLE 5.6

10 mg of salmon calcitonin are dissolved in 1 ml of purified water and emulsified in 10 ml of methylene chloride containing a mixture composed of 1200 mg of poly(dl-lactide-co-glycolide) 50:50 with an inherent viscosity of approximately 0.2 dl/g in $CHCl_3$ and 800 mg of a release-modulating agent, poly(dl-lactide) of molecular weight 2000. For the production of the microspheres, the procedure is as in Example 1. The mean size based on area, obtained by laser light scattering, is 39.8 μm. The efficiency is 86.4%.

EXAMPLE 5.7

51 mg of salmon calcitonin are dissolved in 1 ml of purified water and emulsified in 10 ml of methylene chloride containing a mixture composed of 1200 mg of poly(dl-lactide-co-glycolide) 50:50 with an inherent viscosity of approximately 0.2 dl/g in $CHCl_3$ and 800 mg of a release-modulating agent, poly(dl-lactide) of molecular weight 2000. For the production of the microspheres, the procedure is as in Example 1. The mean size based on area, obtained by laser light scattering, is 32.2 μm. The efficiency is 109.4%.

EXAMPLE 5.8

A solution of 100 μl of salmon calcitonin at a concentration of 12.5% is emulsified in 10 ml of methylene chloride containing 2250 mg of poly(dl-lactide-co-glycolide) 50:50 of inherent viscosity approximately 0.2 dl/g in $CHCl_3$ and 250 mg of a release-modulating agent, poly(dl-lactide) of molecular weight 2000, by means of a sonicator. When the first emulsion has been formed, it is emulsified in its turn in 300 ml of an aqueous solution of polyoxyethylenesorbitan monooleate by means of an Ultraturrax homogenizer for 3 minutes. After this, the suspension is passed through a continuous evaporation system consisting of an incline of appropriate length over which the suspension of microspheres flows in a thin layer, and the microspheres are dried by lyophilization. The mean size based on area, obtained by laser light scattering, is 8 μm. The efficiency is 72.4%.

EXAMPLE 5.9

7.5 mg of salmon calcitonin are dissolved in 1 ml of purified water and emulsified in 10 ml of methylene chloride containing a mixture composed of 150 mg of poly(dl-lactide-co-glycolide) 50:50 with an inherent viscosity of approximately 0.4 dl/g in $CHCl_3$ and 1350 mg of a release-modulating agent, poly(dl-lactide) of molecular weight 2000. For the production of the microspheres, the procedure is as in Example 1. The mean size based on area, obtained by laser light scattering, is 19.7 μm. The efficiency is 95.3%.

EXAMPLE 5.10

10 mg of salmon calcitonin are dissolved in 1 ml of purified water and emulsified in 10 ml of methylene chloride containing a mixture composed of 200 mg of poly(dl-lactide-co-glycolide) 50:50 with an inherent viscosity of approximately 0.2 dl/g in $CHCl_3$ and 1800 mg of a release-modulating agent, poly(dl-lactide) of molecular weight 2000. For the production of the microspheres, the procedure is as in Example 1. The mean size based on area, obtained by laser light scattering, is 33.1 μm. The efficiency is 98.5%.

EXAMPLE 6

Effect on the in vitro release of salmon calcitonin produced by the inclusion of increasing amounts of poly(dl-lactide) of molecular weight 2000 in the polymer matrix of poly(dl-lactide-co-glycolide) 50:50 of inherent viscosity 0.4 dl/g in $CHCl_3$. Percentage of salmon calcitonin released from microspheres in phosphate buffer at pH 7.4 and at 37° C.

| Example | 1 d | 3 d | 4 d | 9 d | 10 d |
|---|---|---|---|---|---|
| 5.1 | — | 0 | 0 | 0.7 | 1.0 |
| 5.2 | — | 1.8 | 2.3 | 5.0 | 5.0 |
| 5.3 | 5.3 | 6.4 | 7.9 | 10.4 | 11.4 |

Effect on the in Example 7 vitro release of salmon calcitonin produced by the inclusion of increasing amounts of poly(dl-lactide) of molecular weight 2000 in the polymer matrix of poly(dl-lactide-co-glycolide) 50:50 of inherent viscosity 0.2 dl/g in $CHCl_3$.

Percentage of salmon calcitonin released from microspheres in phosphate buffer at pH 7.4 and at 37° C.

| Example | 1 d | 4 d | 6 d | 8 d | 10 d |
|---|---|---|---|---|---|
| 5.4 | 0.8 | 0.8 | 0.8 | 1.2 | 2.2 |
| 5.5 | 5.7 | 12.0 | 14.2 | 17.0 | 18.0 |
| 5.6 | 8.9 | 16.1 | 17.7 | 18.9 | 20.9 |

Lastly, as additional examples, a few additional active principles which have been incorporated in microspheres prepared according to the process described in Examples 1 and 2, and which led to the release times shown below, will be mentioned below.

| Active principle | Release time |
| --- | --- |
| Amoxicillin sodium | 1 day to 1 week |
| Naproxen sodium | 1 day to 1 month |
| Salbutamol sulfate | 1 week to 1 month |
| Vinorelbine | 1 week to 1 month |
| Vincristine | 1 week to 1 month |
| Vindesine | 1 week to 1 month |
| Methotrexate | 1 week to 1 month |
| Cisplatin | 1 week to 1 month |
| Carmustine | 1 week to 1 month |
| Doxorubicin | 1 week to 1 month |
| Epirubicin | 1 week to 1 month |
| Daunorubicin | 1 week to 1 month |
| Ifosfamide | 1 week to 1 month |

We claim:

1. Process for preparing a pharmaceutical composition in the form of microspheres affording controlled release of at least one water-soluble active principle, characterized by the following succession of steps:

dissolution of the active principle in water, emulsification of the aqueous solution of active principle thereby obtained with a solution of at least one matrix copolymer of the dl-lactide-co-glycolide type in a chlorinated hydrocarbon containing, in addition, a release-modulating agent which is a low molecular weight polylactide, leading to a first, microfine and homogeneous emulsion, emulsification of said first emulsion thereby obtained in an external aqueous phase containing a surfactant, extraction-evaporation of solvent to obtain microspheres and recovering the same after filtration, washing and drying.

2. Process according to claim 1, characterized in that the active principle is selected from the group consisting of the following substances: calcitonin, vasopressin, somatostatin, growth hormone, prolactin, luteinizing hormone, oxytocin, secretin, salbutamol, gentamicin, tetracycline, tobramycin, amikacin, sodium salicylate, diclofenac sodium, amoxicillin, ampicillin, naproxen sodium, vinorelbine, vincristine, vindesine, methotrexate, cisplatin, carmustine, doxorubicin, epirubicin, daunorubicin, ifosfamide, and derivatives of the foregoing.

3. Process according to claim 1, characterized in that, in said matrix copolymer, the lactic/glycolic ratio is between 75:25 and 50:50.

4. Process according to claim 1, characterized in that the molecular weight of the matrix copolymer is between 10,000 and 250,000.

5. Process according to claim 1, characterized in that the molecular weight of the modulating polylactide is between 1000 and 10,000.

6. Process according to claim 1, characterized in that the ratio of the matrix copolymer to the modulating polylactide is between 10:90 and 90:10.

7. Process according to one of claim 1, characterized in that the water-soluble active principle is dissolved in water to form the internal aqueous phase, without the addition of any substance which might retain the active principle or of any agents to stabilize the emulsion, or any operation intended for increasing the viscosity; in that this phase is emulsified in an organic phase comprising a mixture of said copolymer and said release-modulating agent consisting of a low molecular weight homopolymer of polylactide and said chlorinated hydrocarbon, to prepare the first W/O emulsion; and in that the latter emulsion is added to a third aqueous phase which contains a surfactant, to prepare the second W/O/W emulsion; and in that the solvent is removed rapidly at room temperature and at atmospheric pressure to produce the microspheres.

8. Process according to claim 7, characterized in that said first emulsion is microfine and homogeneous.

9. Process according to claim 7, characterized in that the ratio between the phases of the first emulsion is between 1:100 and 25:100.

10. Process according to claim 7, characterized in that said solvent is rapidly removed, at room temperature and at atmospheric pressure, according to a continuous evaporation system comprising an incline of appropriate length over which the suspension of microspheres flows in a thin layer.

11. Process according to claim 1, characterized in that said chlorinated hydrocarbon is methylene chloride.

12. Process according to claim 1, characterized in that said surfactant is a mixture of polyvinylpyrrolidone and polyoxyethylenesorbitan monooleate.

13. Microspheres obtained by carrying out the process according to claim 1.

14. Microspheres according to claim 13, characterized in that they are 250 μm or less in size.

15. Process according to claim 1, characterized in that the molecular weight of the matrix copolymer is between 12,000 and 34,000.

16. Process according to claim 1, characterized in that the molecular weight of the modulating polylactide is about 2,000.

17. Process according to claim 1, characterized in that the ratio of the matrix copolymer to the modulating polylactide is between 50:50 and 90:10.

18. Process according to claim 10, characterized in that said chlorinated hydrocarbon is methylene chloride.

19. Process according to claim 11, characterized in that said surfactant is a mixture of polyvinylpyrrolidone and polyoxyethylenesorbitan monooleate.

20. Microspheres obtained by carrying out the process according to claim 12.

21. Microspheres according to claim 13, characterized in that they are 125 μm or less in size.

22. Microspheres according to claim 13, characterized in that they are 50 μm or less in size.

23. Microspheres according to claim 20, characterized in that they are 250 μm or less in size.

24. Microspheres according to claim 20, characterized in that they are 125 μm or less in size.

25. Microspheres according to claim 20, characterized in that they are 50 μm or less in size.

26. Process according to claim 1, characterized in that the active principle is selected from the group consisting of the following substances: peptides, bronchodilators, antibiotics, antidepressants, analgesics, anti-inflammatories, and vaccines.

* * * * *

UNITED STATES PATENT AND TRADEMARK OFFICE
CERTIFICATE OF CORRECTION

PATENT NO. : 5,733,567
DATED : March 31, 1998
INVENTOR(S) : R. Arola, et al

It is certified that error appears in the above-identified patent and that said Letters Patent is hereby corrected as shown below:

Column 8, line 48: Insert, centered, -- EXAMPLE 7 --.

Column 8, line 49: Delete "Example 7" in the sentence.

Column 9, line 60: The word "agents" should read -- agent --.

Signed and Sealed this

Sixteenth Day of June, 1998

Attest:

BRUCE LEHMAN

Attesting Officer          Commissioner of Patents and Trademarks